US00PP33874P2

(12) United States Plant Patent
Davasse

(10) Patent No.: US PP33,874 P2
(45) Date of Patent: Jan. 18, 2022

(54) ***CARYOPTERIS* PLANT NAMED 'MINIGOLD'**

(50) Latin Name: ***Caryopteris* x *clandonensis***
Varietal Denomination: Minigold

(71) Applicant: Curoplant Company Ltd., Abbotsford (CA)

(72) Inventor: Jean-Paul Davasse, Angers (FR)

(73) Assignee: Curoplant Company Ltd., Abbotsford (CA)

( * ) Notice: Subject to any disclaimer, the term of this patent is extended or adjusted under 35 U.S.C. 154(b) by 0 days.

(21) Appl. No.: 17/340,904

(22) Filed: Jun. 7, 2021

(51) Int. Cl.
*A01H 5/02* (2018.01)
*A01H 6/50* (2018.01)

(52) U.S. Cl.
USPC ..... Plt./226
CPC ..... *A01H 6/50* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Caryopteris* plant named 'Minigold' that is characterized by its flowers that are lavender blue in color, its rounded and compact plant habit, and its young foliage that is chartreuse in color and mature foliage that is lime green in color.

2 Drawing Sheets

Botanical classification: *Caryopteris* x *clandonensis*.
Cultivar designation: 'Minigold'.

CROSS REFERENCE TO A RELATED APPLICATIONS

This application is related to a Canadian plant breeders' rights application filed Jun. 29, 2020 application No. 20-10275. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Caryopteris* x *clandonensis* and will be referred to hereafter by its cultivar name, 'Minigold'. 'Minigold' represents a new herbaceous perennial grown for landscape use.

The new cultivar of *Caryopteris* arose from a breeding program conducted by the Inventor in Sainte Gemmes sur Loire, France with the goal of developing a *Caryopteris* cultivar with a compact form, colored foliage and intense blue flowers.

'Minigold' originated as a seedling that arose from open pollination of *Caryopteris* x *clandonensis* 'Minbleu' (U.S. Plant Pat. No. 14,674) in 2009. The male parent is presumed to be *Caryopteris* x *clandonensis* 'Jason' (not patented) based on the characteristic of the new cultivar and because it was placed next to the female parent for pollination to occur with no other *Caryopteris* plants in the vicinity. 'Minigold' was selected as a single unique plant in 2010 from amongst the resulting seedlings.

Asexual propagation of the new cultivar was first accomplished by softwood stem cuttings by the Inventor in summer of 2011 in Sainte Gemmes sur Loire, France. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Minigold' as a unique cultivar of *Caryopteris*.

1. 'Minigold' exhibits flowers that are lavender blue in color.
2. 'Minigold' exhibits a rounded and compact plant habit.
3. 'Minigold' exhibits young foliage that is chartreuse in color and mature foliage that is lime green in color.

The female parent of 'Minigold', 'Minbleu', is similar to 'Minigold' in plant habit but differs from 'Minigold' in having foliage that is dark green in color and flowers that are dark blue in color. The probable male parent of 'Minigold', 'Jason', is similar to 'Minigold' in foliage color but differs from 'Minigold' in having a less rounded plant habit. 'Minigold' can also be compared to the *Caryopteris clandonensis* cultivar 'Janice' (U.S. Plant Pat. No. 22,160). 'Janice is similar to 'Minigold' in flower color. 'Janice' differs from 'Minigold' in having a less round plant habit, a shorter plant height, and foliage that is more gold in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosures include but may not be limited by descriptions by Bloomin' Easy, Wayside Gardens, Parkseed, Van Belle Youngplants, Grimms Gardens, Progressive Plants, Jackson and Perkins, Pinterest, Greenleaf Nursery.

BRIEF DESCRIPTION OF THE DRAWINGS

The accompanying color photographs illustrate the overall appearance and distinct characteristics of the new *Caryopteris*. The photographs were taken of a plant three years in age as grown outdoors in a garden in Abbotsford, British Columbia, Canada.

The photograph in FIG. 1 provides a side view of 'Minigold' in bloom.

Figure 1:
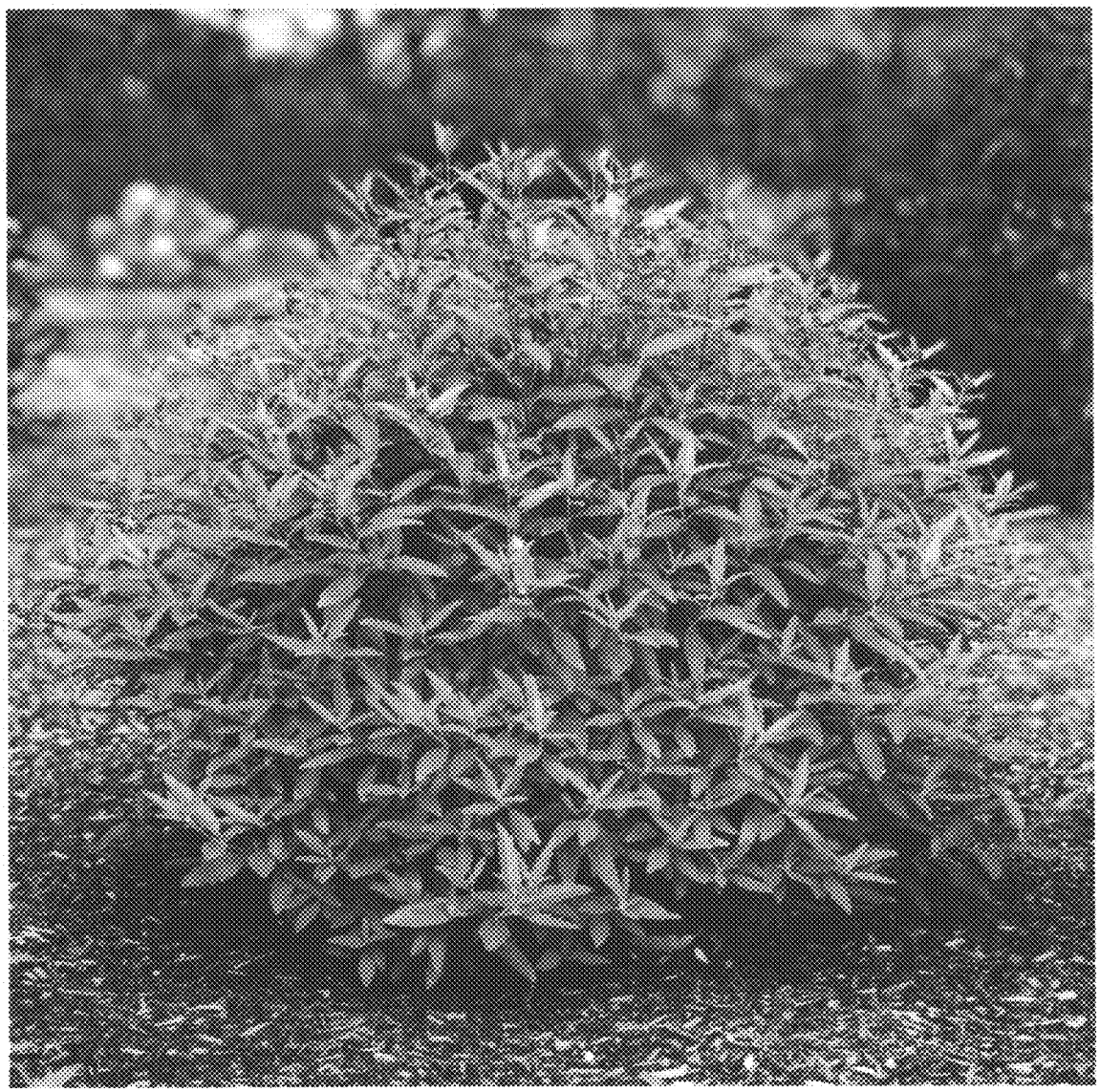
Figure 2:
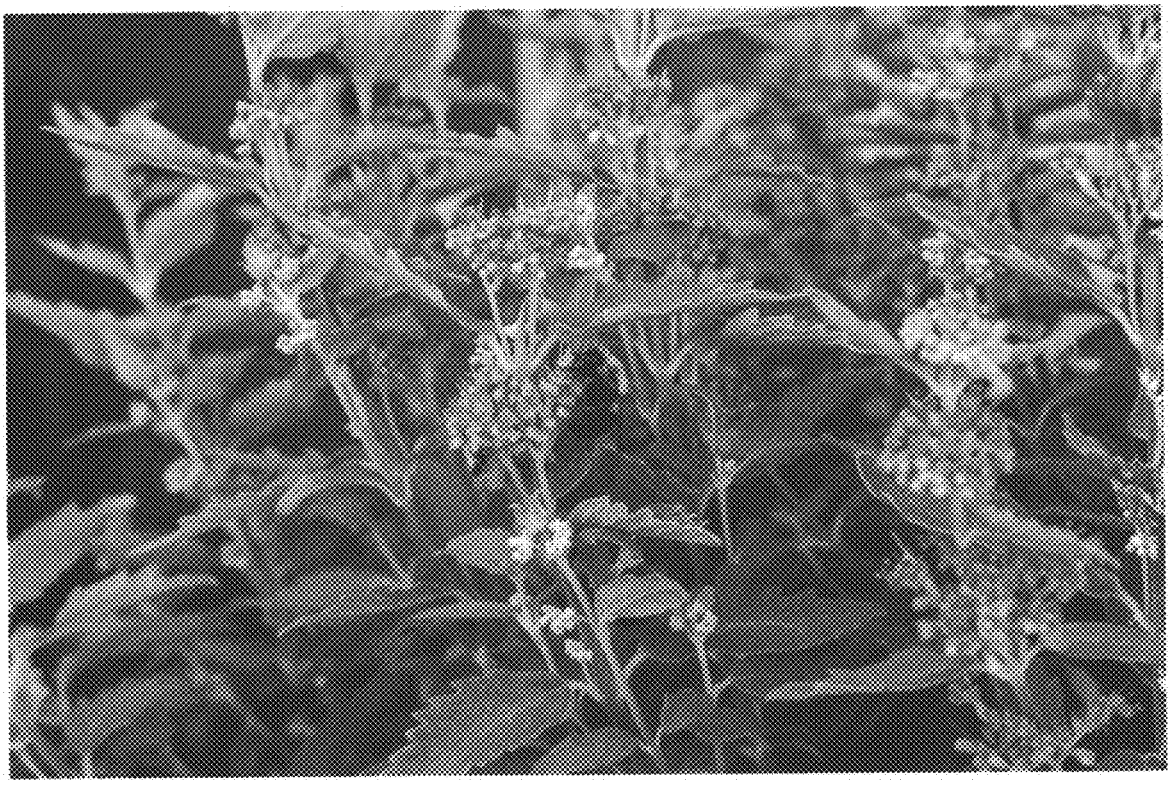

The photograph in FIG. 2 provides a close-up view of the inflorescences of 'Minigold'.

The colors in the photographs may differ slightly from the color values cited in the detailed botanical description, which accurately describe the colors of the new *Caryopteris*.

DETAILED BOTANICAL DESCRIPTION

The following is a detailed description of the new cultivar as observed for plants 18-months in age as grown 2-gallon containers in Abbotsford, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late summer to early fall in Canada.

*Plant type.*—Sub-shrub treated as a perennial.

*Plant habit.*—Rounded and compact.

*Height and spread.*—Average of 63 cm in height, 60 cm in diameter as an 18 month-old plant.

*Hardiness.*—Hardy at least in U.S.D.A. Zones 5 to 8.

*Diseases.*—No susceptibility or resistance to diseases has been observed.

*Growth rate.*—Moderate to highly vigorous.

*Propagation.*—Stem cuttings.

*Root description.*—Fibrous, well-branched.

*Root development.*—Roots initiate in an average of 8 days and fully rooted in a 72-cell liner as a young plant in an average of 6 weeks.

Stem description:

*Shape.*—Round.

*Stem quantity.*—Average of 20 stems, each subdividing into 3 to 5 young stems.

*Stem color.*—Young stems; N186C, older stems; 199A with net-like fissures close to 199B.

*Stem size.*—Average of 6 mm in diameter, 47.2 cm in length.

*Stem surface.*—Matte, moderately covered with very short moderately dense pubescence, average of 0.1 mm in length and 157A in color.

*Stem aspect.*—Upright to semi-upright.

*Branching habit.*—Moderately, freely branching.

*Stem fragrance.*—Pleasantly fragrant when touched.

*Stem strength.*—Moderately strong.

*Internode length.*—2.5 cm.

Foliage description:

*Leaf division.*—Simple.

*Leaf arrangement.*—Opposite.

*Leaf shape.*—Lanceolate.

*Leaf size.*—An average of 3.3 cm in length and 1.5 cm in width.

*Leaf number.*—Average of 22.

*Leaf base.*—Round.

*Leaf apex.*—Subacute.

*Leaf margin.*—Crenate to dentate.

*Leaf venation.*—Pinnate, upper surface; 148B in color, lower surface; 145C in color.

*Leaf surface.*—Upper surface is moderately glossy and slightly rugose, lower surface is matte, upper surface is sparsely pubescent, lower surface is densely covered with very short matted pubescence an average of 0.1 mm in length and 157A in color.

*Leaf color.*—Young upper surface; N144A and 144A, young lower surface; 194A to 194B, mature upper surface; 137B, mature lower surface; 194A to 194B with prominent veins of 145C.

*Leaf attachment.*—Petiolate.

*Leaf petiole.*—Average of 0.7 cm in length, 1 mm in width, 145C in color, surface is densely covered with very short matted pubescence.

*Leaf fragrance.*—Pleasantly fragrant when touched.

Flower description:

*Inflorescence type.*—Terminal and axillary dichasial cymes.

*Lastingness of inflorescence.*—Individual flowers last an average of 12 days, inflorescences last for an average of 5 weeks.

*Flowering stem.*—Average of 26.3 cm in height and 4.2 cm in width.

*Inflorescence size.*—Average of 3.8 cm in height and 4.2 cm in width.

*Inflorescence quantity.*—An average of 11 per stem.

*Flower type.*—Upright to semi-upright, self-cleaning.

*Flower number.*—Average of 500 flowers per lateral stem, 5,500 flowers per plant.

*Flower fragrance.*—Moderate.

*Flower buds.*—Obovate in shape, about 6 mm in length and 2.5 mm in diameter, mature bud; 93C in color.

*Flower size.*—Average of 8 mm in depth, 5 mm in diameter.

*Peduncles.*—Average of 1 cm in length, 1 mm in diameter, angle varying between 0° and 35°, moderate in strength, 145C in color, 197A on sunny-side, pubescent surface.

*Pedicels.*—Average of 2 mm in length, 0.5 mm in diameter, held at an average angle of 25°, moderate in strength, 145C in color, pubescent surface.

*Calyx.*—Campanulate in shape, average of 4 mm in length and 3 mm in diameter.

*Sepals.*—5, elliptic in shape, lower half is fused, both surfaces covered with very short matted pubescence, entire margin, acute apex, 3.5 mm in length, 1.5 mm in width, immature and mature upper surface; 143C, immature and mature lower surface 194C heavily tinged with 93B to 93C.

*Petals.*—5, rotate, lower 75% fused into an irregularly campanulate shape, lower lobe; considerably larger than upper 4 lobes, lower lobe; average of 6 mm in length and 4 mm in width, moderately concave and spathulate in shape, fimbriate margins, upper lobes; 4, average of 4 mm in length and 2.5 mm in width, broadly elliptic in shape, cuspidate apex, entire margin, outer surface finely pubescent, inner surface glabrous, color; when opening and fully open upper (inner) surface 92A, color when opening and fully open lower (outer) surface 93C.

Reproductive organs:

*Gynoecium.*—Pistil; 1, 1.1 cm in length, style; average of 1.05 cm in length, color; N88D, base NN155D, glabrous surface, stigma; bifid, decurrent, N88D in color, glabrous surface, ovary; 1 mm in diameter, N144A in color, glabrous surface.

*Androecium.*—Stamens; 4, filament; average of 1 cm in length, N88C in color, glabrous surface, anthers; dorsifixed and short-oblong in shape, average of 0.75 mm in length, 161A to 161B with 93B along margins, glabrous surface, pollen is sparse (too little to measure color) or absent.

*Fruit.*—Fruit and seed production has not been observed to date.

It is claimed:

1. A new and distinct cultivar of *Caryopteris* plant named 'Minigold' as herein illustrated and described.

* * * * *